US010182970B1

(12) United States Patent
Hassani et al.

(10) Patent No.: US 10,182,970 B1
(45) Date of Patent: Jan. 22, 2019

(54) SECURED AND PROGRAMMABLE MEDICATION DISPENSER

(71) Applicants: Kelly Hassani, Brandon, OR (US); Matthew Hassani, Wildomar, CA (US)

(72) Inventors: Kelly Hassani, Brandon, OR (US); Matthew Hassani, Wildomar, CA (US)

( * ) Notice: Subject to any disclaimer, the term of this patent is extended or adjusted under 35 U.S.C. 154(b) by 0 days.

(21) Appl. No.: 15/943,493

(22) Filed: Apr. 2, 2018

(51) Int. Cl.
*A61J 7/04* (2006.01)
*G16H 20/13* (2018.01)

(52) U.S. Cl.
CPC ........... *A61J 7/0481* (2013.01); *A61J 7/0436* (2015.05); *A61J 7/0454* (2015.05); *G16H 20/13* (2018.01)

(58) Field of Classification Search
CPC ...... A61J 7/0481; A61J 7/0436; A61J 7/0454; G16H 20/13
USPC .................................................. 700/231–244
See application file for complete search history.

(56) References Cited

U.S. PATENT DOCUMENTS 7,295,889 B2 * 11/2007 Lahteenmaki .......... A61J 3/002 700/233
2010/0318218 A1 * 12/2010 Muncy, Jr. ......... B65D 83/0409 700/220
2012/0003928 A1 * 1/2012 Geboers ................ A61J 7/0084 455/41.1
2014/0074283 A1 * 3/2014 Blackburn ............ A61J 7/0076 700/237
2015/0081091 A1 * 3/2015 Blomquist ............. B65D 75/42 700/232
2015/0278478 A1 * 10/2015 Charania ............. G06F 19/3462 700/240
2017/0020785 A1 * 1/2017 McCullough ........... G06F 19/00

* cited by examiner

*Primary Examiner* — Michael Collins
(74) *Attorney, Agent, or Firm* — Plager Schack LLP; Mark H. Plager; Michael J. O'Brien

(57) ABSTRACT

A secured and programmable medical dispenser is configured to distribute medicine according to a schedule. The secured and programmable medical dispenser has a dispenser body mechanically coupled to a dispenser lid with a locking solenoid. A pill tube is arranged within the dispenser body and further has an open pill tube proximal end and a pill tube distal end. A pill release rotary solenoid is attached to the pill tube distal end. A liquid tube is arranged within the dispenser body and further has an open liquid tube proximal end and a liquid tube distal end. A liquid release rotary solenoid is attached to the liquid tube distal end. A microcontroller is attached to the dispenser lid, communicatively coupled to the pill release rotary solenoid and the liquid release rotary solenoid.

4 Claims, 4 Drawing Sheets

SECURED AND PROGRAMMABLE MEDICATION DISPENSER

BACKGROUND

The embodiments herein relate generally to medication dispensers, and more particularly, to a medication dispenser with programming capabilities and a locking system.

Prescription drug abuse has become a large problem. Abuse and/or mistakenly taking drugs at the incorrect time intervals can have catastrophic results.

Therefore, what is needed is a device that dispenses medication as prescribed by the doctor, eliminating or reducing the chances of a person forgetting to take the medication or taking too much of the medication.

SUMMARY

Some embodiments of the present disclosure include a secured and programmable medical dispenser is configured to distribute medicine according to a schedule. The secured and programmable medical dispenser has a dispenser body mechanically coupled to a dispenser lid with a locking solenoid. A pill tube is arranged within the dispenser body and further has an open pill tube proximal end and a pill tube distal end. A pill release rotary solenoid is attached to the pill tube distal end. A liquid tube is arranged within the dispenser body and further has an open liquid tube proximal end and a liquid tube distal end. A liquid release rotary solenoid is attached to the liquid tube distal end. A microcontroller is attached to the dispenser lid, communicatively coupled to the pill release rotary solenoid and the liquid release rotary solenoid.

The microcontroller can be programmed with instructions to receive a medicine distribution schedule for activating the pill release rotary solenoid and the liquid release rotary solenoid. Then activate the pill release rotary solenoid according to the medicine distribution schedule. After that, activate the liquid release rotary solenoid according to the medicine distribution schedule.

In some embodiments, the microcontroller can establish a counter for storing values that are used to perform iterative loops. Those values can include a pill quantity, a pill distribution quantity, a pill distribution schedule, a pill refill quantity, a liquid quantity, a liquid distribution quantity, a liquid distribution schedule, a liquid refill quantity, etc. The microcontroller could have the various solenoids activate while the quantity of the storing value is above a predetermined value which can be set by the user. After each distribution the counter could be iterated downward based on the quantity of medicine distributed.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used as a medication dispenser and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

a. Body
b. Lid
c. Programming Screen
d. Pill Dispenser
e. Liquid Dispenser
f. Lock The various elements of the device of the present disclosure may be related in the following exemplary fashion. It is not intended to limit the scope or nature of the relationships between the various elements and the following examples are presented as illustrative examples only.

Figure 1:
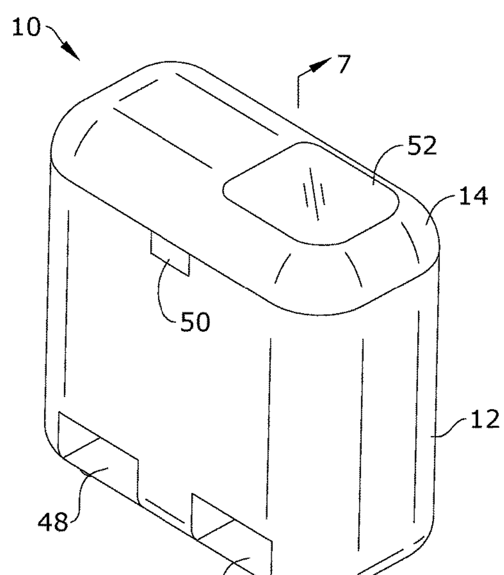
FIG. 1 is a perspective view of one embodiment of the present disclosure.
Figure 2:
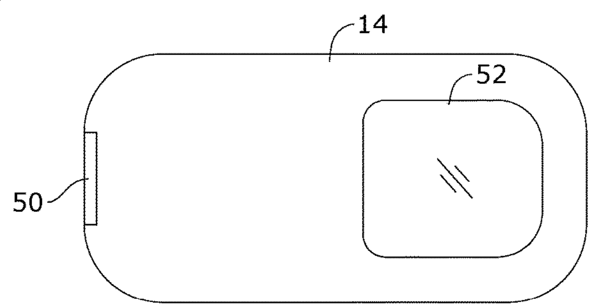
FIG. 2 is a top view of one embodiment of the present disclosure.
Figure 3:
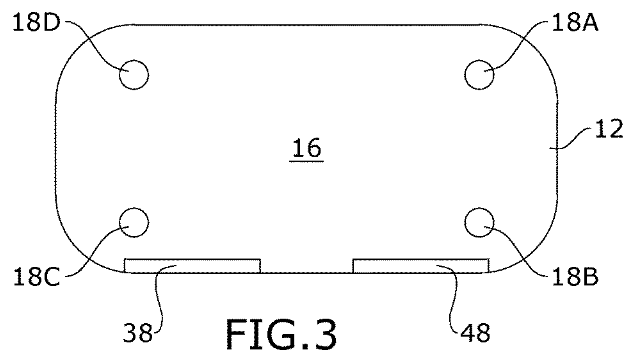
FIG. 3 is a bottom view of one embodiment of the present disclosure.
Figure 4:
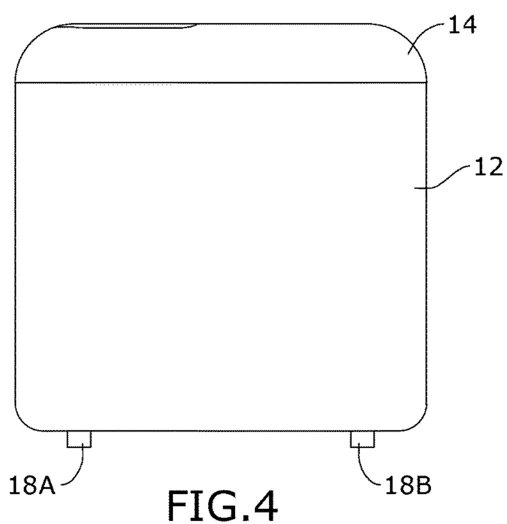
FIG. 4 is a rear view of one embodiment of the present disclosure.
Figure 5:
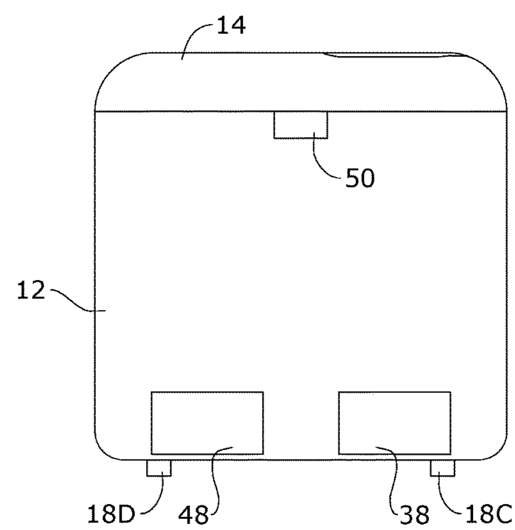
FIG. 5 is a front view of one embodiment of the present disclosure.
Figure 6:
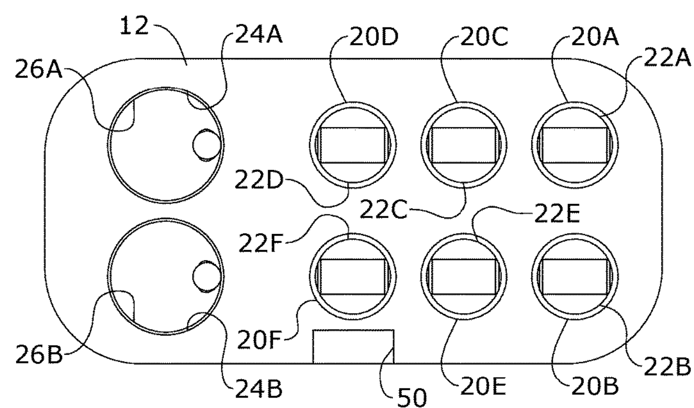
FIG. 6 is a top view of one embodiment of the present disclosure.
Figure 7:
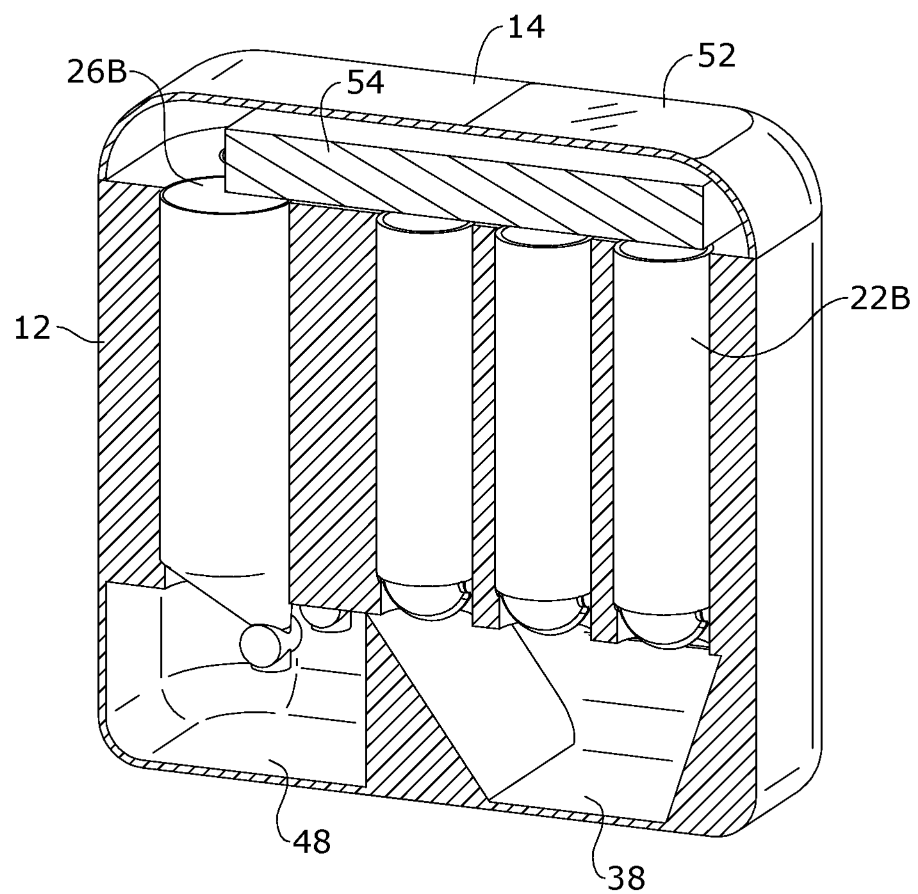
FIG. 7 is a section cutaway view of one embodiment of the present disclosure, taken along line 7-7 in FIG. 1.
Figure 8:
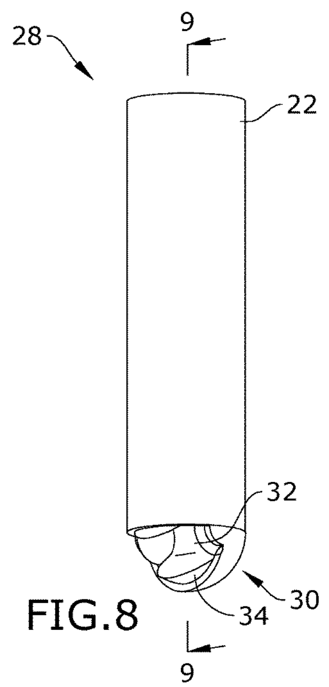
FIG. 8 is a perspective view of one embodiment of the present disclosure.
Figure 9:
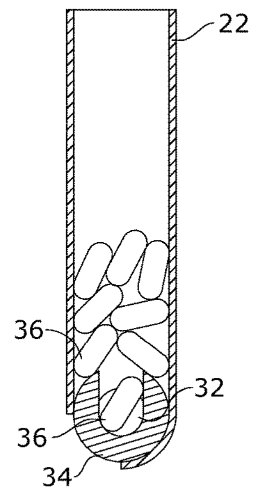
FIG. 9 is a section view of one embodiment of the present disclosure, taken along line 9-9 in FIG. 8.
Figure 10:
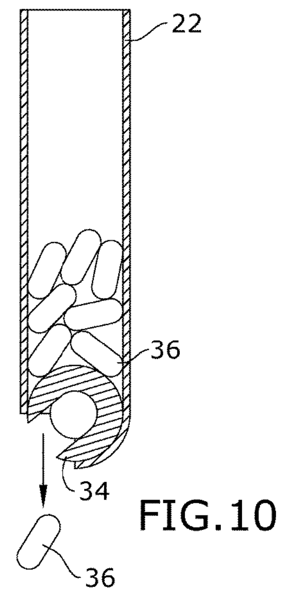
FIG. 10 is a section view of one embodiment of the present disclosure.
Figure 11:
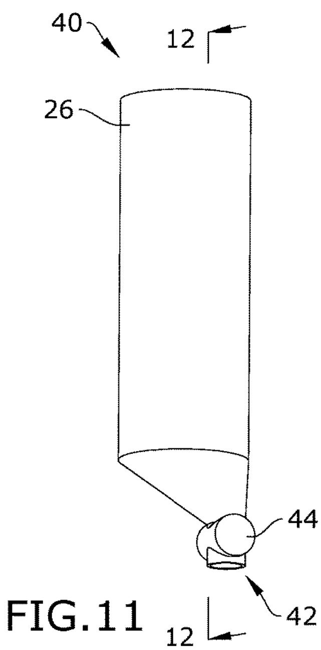
FIG. 11 is a perspective view of one embodiment of the present disclosure.
Figure 12:
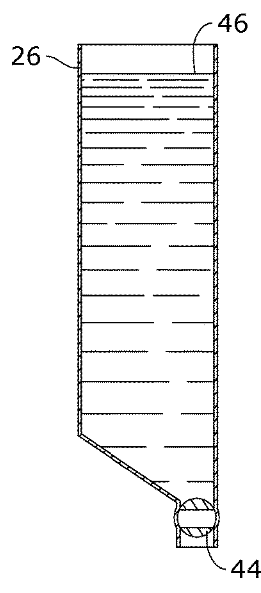
FIG. 12 is a section view of one embodiment of the present disclosure, taken along line 12-12 in FIG. 11.
Figure 13:
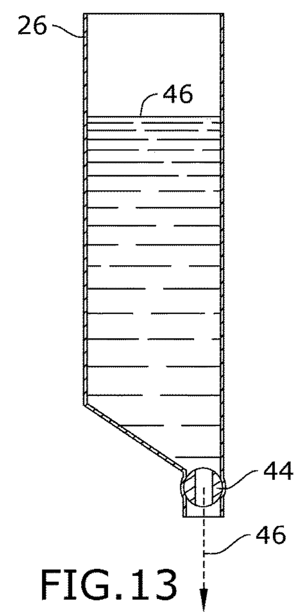
FIG. 13 is a section view of one embodiment of the present disclosure.

By way of example, and referring to FIGS. 1-13, some embodiments of the present disclosure include a secured and programmable medical dispenser 10 further comprising a dispenser body 12 mechanically coupled to a dispenser lid 14. The dispenser body 12 further comprises a bottom surface 16 to which a plurality of feet 18A, 18B, 18C, 18D can be attached.

The dispenser body 12 further comprises a plurality of pill tube slots 20A, 20B, 20C, 20D, 20E, 20F each of which is respectively adapted to accommodate a pill tube 22A, 22B, 22C, 22D, 22E, 22F. The dispenser body 12 further comprises a plurality of liquid tube slots 24A, 24B each of which is respectively adapted to house a liquid tube 26A, 26B.

Turning to these components in more detail, a pill tube 22 further comprises an open pill tube proximal end 28 and a pill tube distal end 30. The pill tube distal end 30 is mechanically coupled to a pill release rotary solenoid 34 with a pill tube rotation attachment point 32. When the pill release rotary solenoid 34 is activate a pill 36 is released from the pill tube distal end 30 to slide down a pill opening 38 in the dispenser body 12

A liquid tube 26 further comprise an open liquid tube proximal end 40 and a liquid tube distal end 42. The liquid tube distal end further comprises a liquid release solenoid 44. When the liquid release solenoid 44 is activated, a liquid 46 is dispensed through the liquid opening 48 in the dispenser body 12.

The dispenser lid 14 is attached to the dispenser body 12 with a lock solenoid 50. The dispenser lid 14 is further attached to a touch screen 52. The touch screen 52 is an input device that is electrically coupled to a microcontroller 54. The microcontroller 54 can be powered with alternating current, direct current or both with an inverter. The microcontroller is communicatively coupled to each pill release rotary solenoid 34, each liquid release solenoid 44 and the lock solenoid 50.

A user communicates to the microcontroller 54 with the touch screen 52 as to which medication is in each pill tube 22 and each liquid tube 24 along with a dispensing schedule. The microcontroller then activates each pill release rotary solenoid 34 and each liquid release solenoid 44 at the appropriate time in order to dispense the requisite quantity of medicine.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A secured and programmable medical dispenser, configured to distribute medicine according to a schedule; the secured and programmable medical dispenser comprising:

a dispenser body mechanically coupled to a dispenser lid with a locking solenoid;

a pill tube, arranged within the dispenser body and further comprising:

an open pill tube proximal end and a pill tube distal end;

a pill release rotary solenoid, attached to the pill tube distal end;

a liquid tube, arranged within the dispenser body and further comprising:

an open liquid tube proximal end and a liquid tube distal end;

a liquid release rotary solenoid, attached to the liquid tube distal end;

a microcontroller, attached to the dispenser lid, communicatively coupled to the pill release rotary solenoid and the liquid release rotary solenoid; and programmed with instructions to:

receive a medicine distribution schedule for activating the pill release rotary solenoid and the liquid release rotary solenoid;

activate the pill release rotary solenoid according to the medicine distribution schedule; and activate the liquid release rotary solenoid according to the medicine distribution schedule.

2. The secured and programmable medical dispenser of claim 1 wherein the microcontroller is further programmed to:

lock the locking solenoid;

receive an unlocking signal;

unlock the locking solenoid.

3. The secured and programmable medical dispenser of claim 1, further comprising a pill tube slot, arranged within the dispenser body and housing the pill tube.

4. The secured and programmable medical dispenser of claim 1, further comprising a liquid tube slot, arranged within the dispenser body and housing the liquid tube.

* * * * *